US006828116B1

(12) United States Patent
Hamilton et al.

(10) Patent No.: US 6,828,116 B1
(45) Date of Patent: Dec. 7, 2004

(54) ENERGY TRANSFER ASSAY METHOD AND REAGENT

(75) Inventors: Alan L. Hamilton, Amersham (GB); Martyn N. Birch, Caerphilly (GB); Malcolm J. Hatcher, Caerphilly (GB); Nigel Bosworth, Cardiff (GB); Brian Scott, Cearphilly (GB)

(73) Assignee: Amersham Biosciences UK Limited, Amersham (GB)

( * ) Notice: Subject to any disclaimer, the term of this patent is extended or adjusted under 35 U.S.C. 154(b) by 0 days.

(21) Appl. No.: 09/719,016

(22) PCT Filed: Jun. 3, 1999

(86) PCT No.: PCT/GB99/01746

§ 371 (c)(1),
(2), (4) Date: Feb. 15, 2001

(87) PCT Pub. No.: WO99/64519

PCT Pub. Date: Dec. 16, 1999

(30) Foreign Application Priority Data

Jun. 11, 1998 (GB) ............................................... 9812596

(51) Int. Cl.[7] ............................ C12Q 1/37; C12Q 1/00; C12Q 1/68; G01N 33/53
(52) U.S. Cl. .............................. 435/23; 435/24; 435/4; 435/6; 435/968; 435/7.72
(58) Field of Search ................................ 435/23, 24, 4, 435/6, 968, 7.72

(56) References Cited

U.S. PATENT DOCUMENTS 5,486,616 A * 1/1996 Waggoner et al. .......... 548/217
5,534,416 A * 7/1996 Millard et al. ................ 345/34
5,658,751 A * 8/1997 Yue et al. ...................... 435/34

FOREIGN PATENT DOCUMENTS

GB 9901746 * 6/1999

* cited by examiner

Primary Examiner—Louise N. Leary
(74) Attorney, Agent, or Firm—Royal N. Ronning, Jr.; Stephen G. Ryan

(57) ABSTRACT

Disclosed is a non-fluorescent cyanine dye that may be used as an acceptor in fluorescence energy transfer assays involving the detection of binding and/or cleavage events in reactions involving biological molecules, and assay methods utilising such dyes. The non-fluorescent cyanine dye is a compound of formula (I), wherein the linker group Q contains at least one double bond and forms a conjugated system with the rings containing X and Y; groups $R^3$, $R^4$, $R^5$ and $R^6$ are attached to the rings containing X and Y, or optionally, are attached to atoms of the $Z^1$ and $Z^2$ ring structures; $Z^1$ and $Z^2$ each represent a bond or the atoms necessary to complete one or two fused aromatic rings each ring having five or six atoms, selected from carbon atoms and, optionally, no more than two oxygen, nitrogen and sulphur atoms; at least one of groups $R^1$, $R^2$, $R^3$, $R^4$, $R^5$, $R^6$ and $R^7$ is a target bonding group; any remaining groups $R^3$, $R^4$, $R^5$, $R^6$ and $R^7$ groups are independently selected from the group consisting of hydrogen, $C_1$–$C_4$ alkyl, $OR^9$, $COOR^9$, nitro, amino, acylamino, quaternary ammonium, phosphate sulphonate and sulphate, where $R^9$ is selected from H and $C_1$–$C_4$ alkyl; any remaining $R^1$ and $R^2$ are selected from $C_1$–$C_{10}$ alkyl which may be unsubstituted or substituted with phenyl, the phenyl being optionally substituted by up to two substituents selected from carboxyl, sulphonate and nitro groups; characterised in that at least one of the groups $R^1$, $R^2$, $R^3$, $R^4$, $R^5$, $R^6$ and $R^7$ comprises a substituent which reduces the fluorescence emission of said dye such that it is essentially non-fluorescent.

18 Claims, 4 Drawing Sheets

SEQUENCE LISTING

```
<160> NUMBER OF SEQ ID NOS: 3

<210> SEQ ID NO 1
<211> LENGTH: 7
<212> TYPE: PRT
<213> ORGANISM: artificial sequence
<220> FEATURE:
<223> OTHER INFORMATION: synthetic peptide

<400> SEQUENCE: 1

Ala Ala Phe Phe Ala Ala Lys
1               5

<210> SEQ ID NO 2
<211> LENGTH: 15
<212> TYPE: DNA
<213> ORGANISM: artificial sequence
<220> FEATURE:
<223> OTHER INFORMATION: synthetic oligonucleotide

<400> SEQUENCE: 2
tacccagacg agcaa                                                    15

<210> SEQ ID NO 3
<211> LENGTH: 15
<212> TYPE: DNA
<213> ORGANISM: artificial sequence
<220> FEATURE:
<223> OTHER INFORMATION: synthetic oligonucleotide

<400> SEQUENCE: 3
ttgctcgtct gggta                                                    15
```

ENERGY TRANSFER ASSAY METHOD AND REAGENT

The present invention relates to the field of fluorescence resonance energy transfer. In particular, the invention relates to fluorogenic assays which include a novel class of non-fluorescent quenching dyes, and to novel quenching dye compounds thereof.

Fluorescence resonance energy transfer (FRET) occurs between the electronic excited states of two fluorophores when they are in sufficient proximity to each other, in which the excited-state energy of the donor fluorophore is transferred to the acceptor fluorophore. The result is a decrease in the lifetime and a quenching of fluorescence of the donor species and a concomitant increase in the fluorescence intensity of the acceptor species. In one application of this principle, a fluorescent moiety is caused to be in close proximity to a quencher molecule. In this configuration, the energy from the excited donor fluorophore is transferred to the quencher and dissipated as heat rather than fluorescence energy.

The use of fluorescence resonance energy transfer (FRET) labels in biological systems is well known. The principle has been used in the detection of binding events or cleavage reactions in assays which employ fluorescence resonance energy transfer. In the case of peptide cleavage reactions, a fluorescent donor molecule and fluorescent acceptor molecule are attached to a peptide substrate on either side of the peptide bond to be cleaved and at such a distance that non-radiative energy transfer between the donor and the acceptor species takes place. For example, EPA 428000 discloses a novel fluorogenic peptide substrate involving a fluorescent donor molecule and a quenching acceptor molecule attached thereto. The labelled substrate can be used in the detection and assay of a viral protease enzyme, whereby, if there is enzyme present in a test sample, the substrate is cleaved and the iikonor and acceptor species are thereby separated. The resultant fluorescent emission of the donor species can be measured. Suitable fluorescent donors include fluorescein derivatives, coumarins and 5-((2-aminoethyl)amino)-naphthalene-1-sulphonic acid (EDANS). Suitable quenching acceptors include 2,4-dinitrophenyl (DNP) and 4-(4-dimethylaminophenyl) azobenzoic acid (DABCYL).

Fluorescence energy transfer has also been used in the study of nucleic acid hybridisation. For example, Tyagi and Kramer (Nature Biotechnology, 14, 303-8, (1996)) disclose homogeneous hybridisation assays which utilise fluorescent labelled probes. The hair-pin probes comprise a single-stranded nucleic acid sequence that is complementary to the target nucleic acid, together with a stem sequence formed from two complementary arms which flank the probe sequence. A fluorophore (EDANS) is attached to one arm and the non-fluorescent quencher moiety (DABCYL) is attached to the complementary arm. In the absence of target, the stem keeps the fluorescent and quenching groups in close proximity causing the fluorescence of the fluorophore to be quenched. When the probe is allowed to bind to a nucleic acid target, it undergoes a conformational change, forming a more stable hybrid with the target and forcing the arm sequences (and the fluorophore and quencher) to move apart. The fluorophore will then emit fluorescence when excited by light of a suitable wavelength.

The success of the fluorescence resonance energy transfer approach is dependent upon the choice of the appropriate donor/acceptor pair. If energy transfer between the donor and acceptor can be optimised, residual fluorescence is minimised when the donor/quencher pair are in close proximity and a large change in signal can be obtained when they are separated. There is an increasing trend towards assay miniaturisation and in high throughput screening assays and, as a result, it is beneficial to use fluorophores with high extinction coefficients in order to achieve the sensitivity levels required. A further problem associated with such assays is due to colour quenching caused by the presence in the assay medium of coloured samples which tend to absorb strongly in the 350–450 nm region of the spectrum.

The present invention provides a non-fluorescent cyanine acceptor dye that can be used as one component of a fluorescent donor/acceptor pair for assays involving the detection of binding and/or cleavage events in reactions involving biological molecules. The fluorescent donor dye possesses a high extinction coefficient, thereby enabling the detection of low levels of the fluorophore. Moreover, the fluorescent dye pair have excitation and emission wavelengths in a range which is substantially free from auto-fluorescence associated with biological samples and from quenching due to coloured samples. Additionally, the dyes are relatively pH insensitive and they possess a high degree of spectral overlap, allowing efficient energy transfer.

Accordingly, the present invention relates to a compound of formula (1):

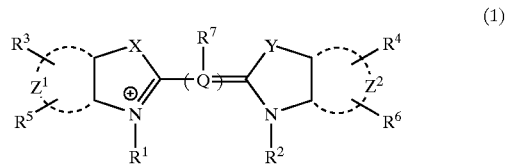

(1)

wherein the linker group Q contains at least one double bond and forms a conjugated system with the rings containing X and Y;

groups $R^3$, $R^4$, $R^5$ and $R^6$ are attached to the rings containing X and Y, or optionally, are attached to atoms of the $Z^1$ and $Z^2$ ring structures;

$Z^1$ and $Z^2$ each represent a bond or the atoms necessary to complete one or two fused aromatic rings each ring having five or six atoms, selected from carbon atoms and, optionally, no more than two oxygen, nitrogen and sulphur atoms;

X and Y are the same or different and are selected from bis-$C_1$–$C_4$ alkyl- and $C_4$–$C_5$ spiro alkyl-substituted carbon, oxygen, sulphur, selenium, —CH=CH— and N—W wherein N is nitrogen and W is selected from hydrogen, a group —$(CH_2)_m R^8$ where m is an integer from 1 to 26 and $R^8$ is selected from hydrogen, amino, aldehyde, acetal, ketal, halo, cyano, aryl, heteroaryl, hydroxyl, sulphonate, sulphate, carboxylate, substituted amino, quaternary ammonium, nitro, primary amide, substituted amide., and groups reactive with amino, hydroxyl, carbonyl, carboxyl, phosphoryl, and sulphydryl groups;

at least one of groups $R^1$, $R^2$, $R^3$, $R^4$, $R^5$, $R^6$ and $R^7$ is a target bonding group;

any remaining groups $R^3$, $R^4$, $R^5$, $R^6$ and $R^7$ groups are independently selected from the group consisting of hydrogen, $C_1$–$C_4$ alkyl, $OR^9$, $COOR^9$, nitro, amino, acylamino, quaternary ammonium, phosphate, suiphonate and sulphate, where $R^9$ is selected from H and $C_1$–$C_4$ alkyl;

any remaining $R^1$ and $R^2$ are selected from $C_1$–$C_{10}$ alkyl which may be unsubstituted or substituted with phenyl the phenyl being optionally substituted by up to two substituents selected from carboxyl, sulphonate and nitro groups;

characterised in that at least one of the groups $R^1$, $R^2$, $R^3$, $R^4$, $R^5$, $R^6$ and $R^7$ comprises a substituent which reduces the fluorescence emission of said dye such that it is essentially non-fluorescent;

provided that the linker group Q is not a squaraine ring system.

Preferably the linker group Q contains 1, 2 or 3 double bonds in conjugation with the rings containing X and Y.

Preferably Q is the group:

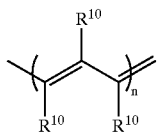

wherein the groups $R^{10}$ are selected from hydrogen and $C_1$–$C_4$ alkyl which may be unsubstituted or substituted with phenyl, or two or more of $R^{10}$ together with the group:

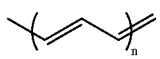

form a hydrocarbon ring system substituted with $R^7$ and which may optionally contain a heteroatom selected from —O—, —S—, or >$NR^7$, wherein $R^7$ is hereinbefore defined; and n=1, 2 or 3.

Suitably, the non-fluorescent cyanine dye for use in the present invention is a compound having the formula (2):

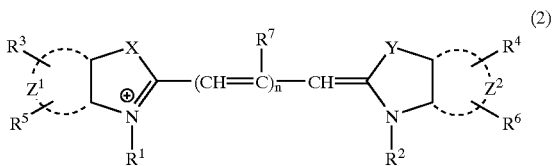

(2)

wherein groups $R^3$, $R^4$, $R^5$ and $R^6$ are attached to the rings containing X and Y or, optionally, are attached to atoms of the $Z^1$ and $Z^2$ ring structures and n is an integer from 1–3;

$Z^1$ and $Z^2$ each represent a bond or the atoms necessary to complete one or two fused aromatic rings each ring having five or six atoms, selected from carbon atoms and, optionally, no more than two oxygen, nitrogen and sulphur atoms;

X and Y are the same or different and are selected from bis-$C_1$–$C_4$ alkyl-and $C_4$–$C_5$ spiro alkyl-substituted carbon, oxygen, sulphur, selenium —CH=CH— and N—W wherein N is nitrogen and W is selected from hydrogen, a group —$(CH_2)_mR^8$ where m is an integer from 1 to 26 and $R^8$ is selected from hydrogen, amino, aldehyde, acetal, ketal, halo, cyano, aryl, heteroaryl, hydroxyl, sulphonate, sulphate, carboxylate, substituted amino, quaternary ammonium, nitro, primary amide, substituted amide, and groups reactive with amino, hydroxyl, carbonyl, carboxyl, phosphoryl, and sulphydryl groups;

at least one of groups $R^1$, $R^2$, $R^3$, $R^4$, $R^5$, $R^6$ and $R^7$ is a target bonding group;

any remaining groups $R^3$, $R^4$, $R^5$, $R^6$ and $R^7$ groups are independently selected from the group consisting of hydrogen, $C_1$–$C_4$ alkyl, $OR^9$, $COOR^9$, nitro, amino, acylamino, quaternary ammonium, phosphate, sulphonate and sulphate, where $R^9$ is selected from H and $C_1$–$C_4$ alkyl;

any remaining $R^1$ and $R^2$ are selected from $C_1$–$C_{10}$ alkyl which may be unsubstituted or substituted with phenyl the phenyl being optionally substituted by up to two substituents selected from carboxyl, sulphonate and nitro groups;

characterised in that at least one of the groups $R^1$, $R^2$, $R^3$, $R^4$, $R^5$, $R^6$ and $R^7$ comprises a substituent which reduces the fluorescence emission of said dye such that it is essentially non-fluorescent.

Suitably at least one of the groups $R^1$, $R^2$, $R^3$, $R^4$, $R^5$, $R^6$ and $R^7$ of the dyes according to the present invention comprises a substituent which reduces the fluorescence emission of the dye such that it is essentially non-fluorescent. Suitably, at least one of groups $R^3$, $R^4$, $R^5$, $R^6$ and $R^7$ of the non-fluorescent cyanine dyes of structures (1) and (2) is a nitro group which may be attached directly to the rings containing X and Y. In the alternative, a mono- or di-nitro-substituted benzyl group may be attached to the rings containing X and Y, which optionally may be further substituted with one or more nitro groups attached directly to the aromatic rings. Preferably, at least one of groups $R^1$, $R^2$, $R^3$, $R^4$, $R^5$, $R^6$ and $R^7$ of the non-fluorescent cyanine dyes of structures (1) and (2) comprises at least one nitro group.

The target bonding group $R^1$, $R^2$, $R^3$, $R^4$, $R^5$, $R^6$ and $R^7$ can be any group suitable for attaching the non-fluorescent cyanine dye to a target material, such as a carrier material or a biological compound and as such will be well known to those skilled in the art. For example, the target bonding group may be a reactive group for reacting with a functional group on the target material. Alternatively, the target bonding group may be a functional group and the target may contain the reactive constituent.

Preferably, the target bonding group is of the structure—E—F where E is a spacer group and F is the reactive or functional group. A reactive group of the dye can react under suitable conditions with a functional group of a target molecule; a functional group of the dye can react under suitable conditions with a reactive group of the target molecule, whereby the target molecule becomes labelled with the dye.

Preferably, the reactive group F is selected from carboxyl, succinimidyl ester, sulpho-succinimidyl ester, isothiocyanate, maleimide, haloacetamide, acid halide, hydrazide, vinylsulphone, dichlorotriazine and phosphoramidite. Preferably, the functional group F is selected from hydroxy, amino, sulphydryl, imidazole, carbonyl including aldehyde and ketone, phosphate and thiophosphate. By virtue of these reactive and functional groups the non-fluorescent cyanine dye may be reacted with and covalently bound to target materials.

Suitable spacer groups may contain 1–60 chain atoms selected from the group consisting of carbon, nitrogen, oxygen, sulphur and phosphorus. For example the spacer group may be:

—$(CHR')_p$—

—$\{(CHR')_q$—O—$(CHR')_r$—$\}_s$—

—$\{(CHR')_q$—NR'—$(CHR')_r$—$\}_s$—

—$\{(CHR')_q$—(CH=CH)—$(CHR')_r$—$\}_s$—

—$\{(CHR')_q$—Ar—$(CHR')_r$—$\}_s$—

—{(CHR')$_q$—CO—NR'—(CHR')$_r$—}$_s$—
—{(CHR')$_q$—CO—Ar—NR'—(CHR')$_r$—}$_s$—
where R' is hydrogen, or $C_1$–$C_4$ alkyl which may be optionally substituted with suiphonate, Ar is phenylene, optionally substituted with sulphonate, ρ is 1–20, preferably 1–10, q is 1–5, r is 0–5 and s is 1–5.

Specific examples of reactive groups $R^1$–$R^7$ and the groups with which $R^1$–$R^7$ can react are provided in Table 1. In the alternative, the $R^1$–$R^7$ may be the functional groups of Table 1 which would react with the reactive groups of a target molecule.

TABLE 1

Possible Reactive Substituents and Functional Groups Reactive Therewith

| Reactive Groups | Functional Groups |
| --- | --- |
| succinimidyl esters | primary amino, secondary amino |
| anhydrides, acid halides | primary amino, secondary amino, hydroxyl |
| isothiocyanate | amino groups |
| vinylsulphone | amino groups |
| dichlorotriazines | amino groups |
| haloacetamides, maleimides | thiols, imidazoles, hydroxyl, amines |
| carboxyl | amino, hydroxyl, thiols |
| phosphoramidites | hydroxyl groups |

Particularly suitable reactive groups $R^1$–$R^7$ which are especially useful for labelling target components with available amino and hydroxyl functional groups include:

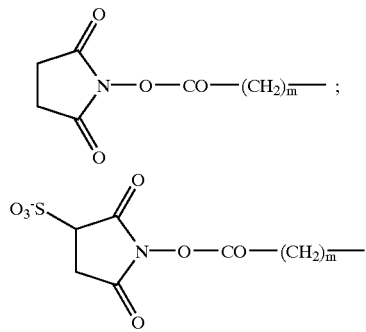

where m is an integer from 1–10.

Aryl is an aromatic substituent containing one or two fused aromatic rings containing 6 to 10 carbon atoms, for example phenyl or naphthyl, the aryl being optionally and independently substituted by one or more substituents, for example halogen, straight or branched chain alkyl groups containing 1 to 10 carbon atoms, aralkyl and alkoxy for example methoxy, ethoxy, propoxy and n-butoxy.

Heteroaryl is a mono- or bicyclic 5 to 10 membered aromatic ring system containing at least one and no more than 3 heteroatoms which may be selected from N, O, and S and is optionally and independently substituted by one or more substituents, for example halogen, straight or branched chain alkyl groups containing 1 to 10 carbon atoms, aralkyl and alkoxy for example methoxy, ethoxy, propoxy and n-butoxy.

Aralkyl is a $C_1$–$C_6$ alkyl group substituted by an aryf or heteroaryl group.

Halogen and halo groups are selected from fluorine, chlorine, bromine and iodine.

The non-fluorescent cyanine dyes for use in the present invention may also include water solubilising constituents attached thereto for conferring a hydrophilic characteristic to the dye. They may be attached directly to the aromatic ring system of the cyanine dye or they may be attached to the spacer group E. Suitable solubilising constituents may be selected from the group consisting of sulphonate, sulphate, phosphonate, phosphate, quaternary ammonium and hydroxyl. Sulphonate or sulphonic acid groups attached directly to the aromatic ring of the non-fluorescent quenching dye are to be particularly preferred. Water solubility may be necessary when labelling proteins.

In a second aspect, the present invention relates to a biological material labelled with a non-fluorescent cyanine dye.

In a further aspect, the invention relates to a biological material which comprises two components one of which is labelled with a fluorescent dye which may act as a donor of resonance energy and the other with a non-fluorescent cyanine dye which may act as an acceptor of resonance energy transferred from the donor.

In a still further aspect, the invention relates to an assay method which comprises:

i) separating two components which are in an energy transfer relationship, the first component being labelled with a fluorescent donor dye and the second component being labelled with a non-fluorescent cyanine acceptor dye; and, ii) detecting the presence of the first component by measuring emitted fluorescence.

In a still further aspect the invention relates to an assay method which comprises:

i) binding one component of a specific binding pair with a second component of said pair, said first component being labelled with a fluorescent donor dye and said second component being labelled with a non-fluorescent cyanine acceptor dye to bring about an energy transfer relationship between said first and second components; and, ii) detecting the binding of the first and second components by measuring emitted fluorescence.

The non-fluorescent cyanine dyes of the present invention are employed as acceptor dyes in assay methods utilising fluorescence resonance energy transfer. When a non-fluorescent cyanine dye of the invention is in an energy transfer relationship with a fluorescent donor dye, the fluorescence emission of the donor is reduced through quenching by the acceptor. When resonance energy transfer is lost through separation of the fluorescent donor dye and the acceptor dye, the fluorescence emission due to the donor dye is restored Effective non-fluorescent quenching dyes have a low efficiency for converting absorbed incident light into fluorescence and, as such, are unsuitable as fluorescent labels where a high degree of sensitivity is required. The relative effectiveness of the non-fluorescent cyanine dyes as quencher dyes is illustrated in FIG. 1 which shows the relative fluorescence emission of representative non-fluorescent cyanine dyes of the invention compared with corresponding dyes of the same class and with similar absorption characteristics in the visible region of the spectrum.

The intrinsic fluorescence of the cyanine dyes of the present invention, when they are employed as energy acceptors is preferably less than 10% of the fluorescence emission of the donor dye upon excitation at the donor excitation wavelength and detection of emission at the donor emission wavelength. FIG. 3 shows the decrease in background signal obtainable by the use of Compound II and Compound XI as acceptor dyes compared with that of a standard matched fluorescent cyanine acceptor dye (Cy5), when measured at the emission maxima of the donor dye. The contribution to background fluorescence is thus minimised by the use of the non-fluorescent cyanine dyes of the invention as quencher dyes. Moreover, the present dyes are designed such that their spectral overlap with a fluorescent donor dye is maximised, thereby improving efficiency of quenching.

The biological material can be a biological molecule which may be cleaved into the two component parts; or the biological material may comprise two components as hereinbefore defined which may be bound either by covalent or non-covalent association.

The present invention therefore relates to a novel fluorogenic substrate and an assay method for the detection and measurement of the cleavage of a molecule into two component parts, the first component being labelled with a fluorescent donor dye in an energy transfer relationship with a non-fluorescent cyanine acceptor dye bound to the second component.

The assays may be performed according to the present invention in high throughput screening applications, including those in which compounds are to be screened for their inhibitory effects, potentiation effects, agonistic, or antagonistic effects on the reaction under investigation. Examples of such assays include, but are not restricted to, the cleavage of a peptide or protein by a protease and the cleavage of a DNA or RNA molecule by a nuclease. In this assay format, the enzyme substrate (peptide or nucleic acid) will include a sequence whose structure combines a fluorescent donor dye molecule with the non-fluorescent cyanine acceptor dye, attached to the substrate at either side of the substrate bond to be cleaved. The substrate joins the fluorescent donor and the acceptor moieties in close proximity. The intrinsic fluorescence of the donor is reduced through quenching by the acceptor due to resonance energy transfer between the pair of dyes. Resonance energy transfer becomes insignificant when the distance between the donor and acceptor moieties is greater than about 100 Angstroms. Cleavage of the substrate results in the separation between donor and acceptor dyes and concomitant loss of resonance energy transfer. The fluorescence signal of the donor fluorescent dye increases, thereby enabling accurate measurement of the cleavage reaction.

Briefly, an assay for the detection of proteolytic enzyme activity may be configured as follows. A reaction mixture is prepared by combining a protease enzyme and a fluorogenic substrate which combines a fluorescent donor dye molecule with a non-fluorescent acceptor dye of formula (2) attached to the substrate at either side of the substrate bond to be cleaved. A known or a putative protease inhibitor compound may be optionally included in the reaction mixture. Typically the reaction is performed in buffered solution and the reaction is allowed to proceed to completion. The progress of the reaction may be monitored by observing the steady state fluorescence emission due to the fluorescent donor dye, which is recorded using a spectrofluorimeter.

Alternatively, the invention relates to an assay method for detecting and measuring binding, by covalent or non-covalent association, of one component of a ligand/reactant pair with a second component of said pair, said first component being labelled with a fluorescent donor dye and said second component being labelled with a non-fluorescent cyanine acceptor dye. Such assays are conveniently categorised as one of two types.

i) The first category comprises equilibrium binding assays, in which one component of a specific binding pair binds non-covalently to a second component of the specific binding pair. Such equilibrium binding assays may be applied to screening assays in which samples containing compounds to be screened are tested for their effect upon the binding of the first component of the specific binding pair (either antagonistic or agonistic), to the second component. Either component may be labelled with the donor dye or the acceptor dye. In the absence of binding, the labelled components are too far apart for resonance energy transfer to occur. Upon binding of one labelled component to its labelled specific binding partner, the label moieties are brought into sufficiently close proximity for energy transfer to occur between donor and acceptor species resulting in a quenching of the donor fluorescence and a decrease in donor fluorescent signal.

For example, the dyes used in the present invention can be used to label probes such as those described by Tyagi and Kramer (loc. cit.) for use in the detection and identification of unique DNA sequences or specific genes in a complete DNA molecule or mixtures of nucleic acid fragments. One end of the nucleic acid probe is labelled with a fluorescent dye and at the other end with a non-fluorescent cyanine acceptor dye. In the absence of specific target sequence, the fluorescent and quenching species will be held sufficiently close for energy transfer to occur. Consequently, irradiation of the fluorophore by excitation light will give reduced fluorescent signal. Interaction of the probe with a specific target nucleic acid sequence causes a conformational change to take place in the probe, such that the fluorescent donor and acceptor become separated by distance. Excitation of the fluorophore will result in a fluorescent signal which may be recorded using a spectrofluorimeter.

Alternatively, the equilibrium binding assay may employ a sandwich assay format in which one component of a specific binding pair, such as a first antibody, is coated onto the wells of a microtitre well plate. Following binding of an antigen to the first antibody, a second antigen-specific antibody is then added to the assay mix, so as to bind with the antigen-first antibody complex; In this format, either the first antibody or the antigen may be labelled with the donor dye and the second antibody labelled with the acceptor dye or vice versa. In the absence of binding of the first antibody-antigen-second antibody complex, the labelled components are too far apart for resonance energy transfer to occur. Upon binding of the second antibody with the first antibody-antigen complex, the label moieties are brought into sufficiently close proximity for energy transfer to occur between donor and acceptor species resulting in a quenching of the donor fluorescence and a decrease in donor fluorescent signal. Fluorescence signal is measured and the concentration of antigen may be determined by interpolation from a standard curve.

Examples of specific binding pairs include, but are not restricted to, antibodies/antigens, lectins/glycoproteins, biotin/(strept)avidin, hormone/receptor, enzyme/substrate or co-factor, DNA/DNA, DNA/RNA and DNA/binding protein. It is to be understood that in the present invention, any molecules which possess a specific binding affinity may be employed, so that the energy transfer dyes of the present invention may be used for labelling one component of a specific binding pair, which in turn may be used in the detection of binding to the other component.

ii) In the second category, the assay may comprise detection and measurement of the addition of a fluorescent donor dye labelled moiety (the reactant) in solution in the assay medium to a non-fluorescent acceptor dye-labelled moiety (the substrate) or vice versa, by covalent attachment mediated through enzyme activity. Examples of such assays include, but are not restricted to, the joining of DNA or RNA molecules to other nucleic acid molecules by ligases, the addition of a nucleotide to a DNA or RNA molecule by a polymerase and the transfer of a labelled chemical moiety from one molecule to another by a transferase such as acetyl transferase. A known or a putative enzyme inhibitor may be optionally included in the reaction mixture. It is to be understood that any two appropriate reactant and substrate moieties may be employed. Either of the donor or the acceptor dyes of the present invention may be used for labelling one moiety which in turn may be used in the detection and measurement of the reaction with the substrate.

For example, in a DNA ligation assay, DNA molecules to be joined are mixed together in aqueous buffer containing ATP in the presence of a DNA ligase. Following incubation, the DNA strands are covalently attached in the correct configuration by the formation of standard phosphodiester linkages in both strands of the duplex. Upon joining the label moieties are bought into sufficiently close proximity for energy transfer to occur between donor and acceptor species resulting in a quenching of the donor fluorescence and a signal decrease which is proportional to the amount of ligated product formed.

The invention also relates to labelling methods wherein the non- fluorescent cyanine dyes of structures (1) and (2) including at least one reactive or functional group at the $R^1$–$R^7$ positions covalently react with amino, hydroxyl, aidehyde, phosphoryl, carboxyl, sulphydryl or other reactive groups on target materials. Such target materials include, but are not limited to the group consisting of antigen, antibody, lipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl, hydroxyl and carboxyl, phosphate and thiophosphate groups, microbial materials, drugs and toxins.

The selection of suitable fluorescent donor and acceptor pairs is generally dependent on several factors.

i) Firstly, the donor and acceptor chromophores should have strong electronic transitions in the near UV to near IR spectral range.
ii) Secondly, the donor and acceptor moieties should be in relatively close proximity with each other. Suitably the donor and acceptor species should be in the range 10 –100 Angstroms.
iii) Thirdly, there should be a suitable overlap between the donor emission spectrum and absorption spectrum of the acceptor. The greater the overlap between donor emission spectrum and the excitation spectrum of the acceptor, the greater the energy transfer. Energy transfer can occur between dyes which share minimal spectral overlap, but this is only observed when the dyes are in close proximity.

Suitable fluorescent donor dyes that can be combined with the non-fluorescent cyanine acceptor dyes to form energy transfer pairs for the practice of the present invention include the well known reactive analogues of the fluorescein, rhodamine and cyanine dyes. Other low molecular weight fluorescent dyes may be selected from the derivatives of the bis-pyrromethine boron difluoride dyes, such as 3,3',5,5'-tetramethyl-2,2'-pyrromethine-1,1'-boron difluoride, sold under the trademark BODIPY by Molecular Probes Inc. Particularly preferred are the cyanine dyes.

Suitable fluorescein donor dyes include: 5- and 6-carboxyfluorescein and 6-carboxy-4',5'-dichloro-2',7'-dimethoxyfluorescein. Suitable rhodamine dyes include: 6-carboxyrhodamine (Rhodamine 110), 5-carboxyrhodamine-6G (R6G-5 or REG-5), 6-carboxyrhodamine-6G (R6G-6 or REG-6), N,N,N',N'-tetramethyl-6-carboxyrhodamine (TAMRA or TMR), 6-carboxy-X-rhodamine (ROX). Suitable cyanine donor dyes include the CyDyes™: Cy3, Cy3.5, Cy5, Cy5.5 and Cy7. (CyDye and Cy are trademarks of Amersham Pharmacia Biotech UK Limited.) Cyanine dyes suitable for use as the donor component in the assay of the present invention are disclosed in U.S. Pat. No. 5268486 (Waggoner et al), or the rigidised cyanine dyes such as those disclosed in GB Patent No.2301832 (Waggoner et al). Alternatively the fluorescent donor species used as the donor component may be a fluorescence energy transfer dye cassette. Examples of such fluorescence energy transfer dye cassettes are to be found in GB Patent No.2301833 (Waggoner et al).

Table 2 below shows examples of fluorescent donor dyes and corresponding non-fluorescent cyanine acceptor dyes which are suitable for use in the methods according to the present invention.

TABLE 2

| Donor | Acceptor |
|---|---|
| Cy3 | 2-{5-[1-(5-carboxypentyl)-3,3-dimethyl-5-sulpho-1,3-dihydro-2H-indol-2-ylidene]-1,3-pentadienyl}-1-ethyl-3,3-dimethyl-5-nitro-3H-indolinium (Compound I) * |
| Cy3.5 | |
| Cy5 | 2-{5-[1-(5-carboxypentyl)-3,3-dimethyl-5-sulpho-1,3-dihydro-2H-indol-2-ylidene]-1,3-pentadienyl}-1-(3,5-dinitrobenzyl)-3,3-dimethyl-5-nitro-3H-indolinium (Compound II) * |
| | 1-butyl-2-{5-[1-(5-carboxypentyl)-3,3-dimethyl-6-sulpho-1,3-dihydro-2H-benzo[e]indol-2-ylidene]-1,3-pentadienyl}-3,3-dimethyl-5-nitro-3H-indolinium (Compound III) * |
| | 1-butyl-2-{7-[1-(5-carboxypentyl)3,3-dimethyl-5-sulpho-1,3-dihydro-2H-indol-2-ylidene]-1,3,5-heptatrienyl}-3,3-dimethyl-5-nitro-3H-indolinium (Compound IV) * |
| Cy5.5 | 1-butyl-2-{7-[1-(5-carboxypentyl)3,3-dimethyl-5-sulpho-1,3-dihydro-2H-indol-2-ylidene]-1,3,5-heptatrienyl}-3,3-dimethyl-5-nitro-3H-indolinium (Compound IV) * |

* salt form, undefined.

The non-fluorescent cyanine dyes of formulae (1) and (2) may be prepared by a process comprising:

a) reacting a first compound having the formula (A):

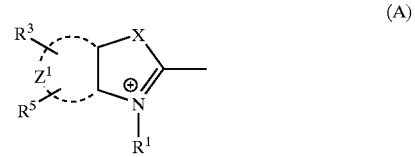

(A)

where X, $Z^1$, $R^1$, $R^3$ and $R^5$ are hereinbefore defined, b) a second compound which is the same or different from the first compound and having the formula (B):

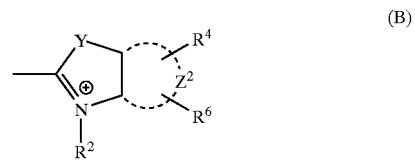

(B)

where Y, $Z^2$ $R^2$, $R^4$, $R^6$ are hereinbefore defined, and c) a third compound suitable for forming a linkage between the first and second compounds, wherein a), c)

and b) are reacted either in a two-or single step process to form the compounds of formulae (1) and (2).

In the case of a two step synthesis, an intermediate dye compound is first formed by reacting an indolenine compound of structure (A) with a compound suitable for forming the linkage wherein the reaction is performed in a suitable polar solvent such as ethanol or acetic acid. In the second stage, the intermediate dye is reacted with the second indolenine compound of structure (B) in a medium such as pyridine, acetic acid and acetic anhydride at room temperature. Such reaction conditions are also suitable for the preparation of non-fluorescent cyanine dyes of the present invention by a one step process. Reagents c) which may be used for forming the linkage between the indolenine moieties are those suitable for forming a polymethine chain. Reagents and methods suitable for forming cyanine dyes containing polymethine linkages will be well known to those skilled in the art and include triethyl orthoformate, malondialdehyde bis-(phenylimine) hydrochloride and N-{(5-phenylamino)-2,4-pentadienylidene}aniline hydrochloride. (See for example, Fry D. J, Cyanine Dyes and Related Compounds, in Rodd's Chemistry of Carbon Compounds, Elsevier 1977, page 369–422).

The non-fluorescent cyanine dyes of the present invention may be used to covalently label a target material such as a component of the assay system as hereinbefore described. Covalent labelling using compounds of the present invention may be accomplished with a target having at least one functional or reactive group as hereinbefore defined. The target may be incubated with an amount of a compound of the present invention having at least one of $R^1$–$R^7$ that includes a reactive or functional group as hereinbefore defined that can covalently bind with the functional or reactive group of the target material. The target material and the compound of the present invention are incubated under conditions and for a period of time sufficient to permit the target material to covalently bond to the compound of the present invention.

BRIEF DESCRIPTION OF DRAWINGS

The invention is further illustrated by reference to the following examples and figures.

Figures

EXAMPLES

Example 1

Figure 1A:
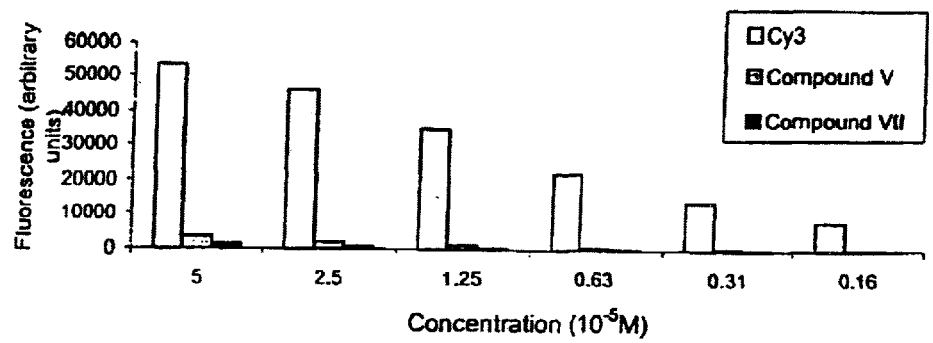
FIG. 1 illustrates the relative fluorescence emission of Cy3 and Compounds V and VII (FIG. 1a) and of Cy5 and Compounds IX and XI (FIG. 1b) according to Example 12.
Figure 1B:
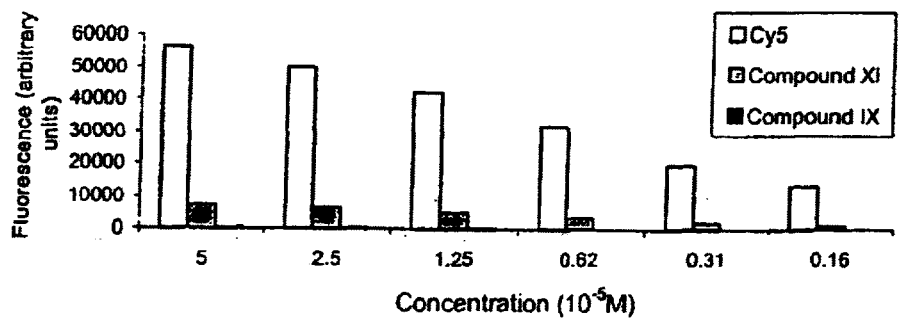

Preparation of 2-{5-[1-(5-Carboxypentyl)-3,3-dimethyl-5-sulpho-1,3-dihydro-2H-indol-2-ylidene]-1,3-pentadienyl}-1-ethyl-3,3-dimethyl-5-nitro-3H-indolinium, Salt (Compound I)

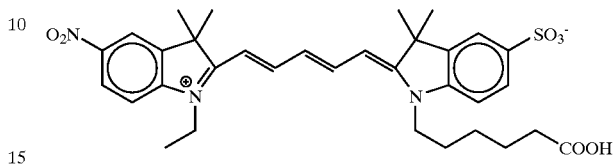

i) 5-Nitro-2,3,3-trimethylindole

Sodium nitrate (3.84 g, 45.2 mmol) was dissolved in concentrated sulphuric acid (100 ml). After cooling in ice, this solution was added to a solution of 2,3,3-trimethylindole (6.65 g, 41.8 mmol) in concentrated sulphuric acid (100 ml) such that the temperature was maintained in the range 0–5° C. The reaction was stirred at 0–5° C. for 90 minutes after completing the addition, then allowed to warm to room temperature and stirred for a further 16 hours. The mixture was poured onto ice (200 g) then made basic by the addition of 50% aqueous sodium hydroxide solution to pH12 (pH paper). The crude product was collected by filtration and washed with water until the washings were neutral (~1000 ml). The off-yellow solid was dried at the pump, dissolved in ethyl acetate (250 ml) and dried further ($MgSO_4$). The solution was filtered and the red filtrate was rotary evaporated to dryness. The solid was dissolved in chloroform-:ethyl acetate (95:5, 30 ml) and purified by silica flash chromatography. This gave a dark yellow solid, 5.12 g, 25 mmol, 60% yield. UV analysis (methanol) showed a single peak with λmax=300 nm. Mass spectrometry (MALDI-TOF with a gentisic acid matrix) gave m/z=203.8 (for $C_{11}H_{12}N_2O_2$=204.23). $^1$H NMR:δ=1.97 (s, 6H), 2.95 (s, 3H), 8.58 (d, J=10 Hz, 1H), 8.70 (s, 1H), 8.78 (d, J=10 Hz, 1H).

ii) 1-Ethyl-5-nitro-2,3,3-trimethylindolium iodide

5-Nitro-2,3,3-trimethylindole (518 mg, 2.54 mmol) and ethyl iodide (2.5 ml, 4.85 g, 31 mmol, excess) were mixed and heated to reflux for 8 hours. After cooling to room temperature the excess ethyl iodide was removed by a gentle nitrogen stream and the residue was dissolved in chloroform and filtered through a plug of silica. The silica was washed with chloroform (1 volume) and the combined filtrates were rotary evaporated to give the product as a yellow oil, (486 mg, 1.35 mmol, 53% yield).

iii) 1-(5-Carboxypentyl)-5-sulpho-2,3,3-trimethylindolium bromide

To 5-sulpho-2,3,3-trimethylindole (potassium salt) (5.0 g, 18 mmol) was added 6-bromohexanoic acid (10.56 g, 53.8 mmol) in 1,2-propanediol (15 ml) and heated at 80° C. for 72 hours. The mixture was cooled and diluted with water (60 ml) and a solution of NaOH (10% in water, 60 ml) with stirring. The product was purified using preparative HPLC (Dynamax, $C_{18}$ column, gradient of $TFA/H_2O$ to TFA/MeCN) to yield a grey/pink solid (2.4 g, 28%).

iv) 2-(4-Anilinobuta-1,3-dienyl)-1-(5-carboxypentyl)-3,3-dimethyl5-sulpho-indolium, salt To the product from stage iii) (400 mg, 0.85 mmol) was added malondialdehyde bis-(phenylimine) HCl (322 mg, 1.24 mmol) in acetic acid (5 ml) and the mixture heated at 140° C. for 16 hours with stirring. The product was purified by HPLC (C$_4$ column, TFA/H$_2$O to TFA/MeCN gradient) to yield a red/grey solid (194.4 mg, 38%).

v) Synthesis of Compound (I)

1-Ethyl-5-nitro-2,3,3-trimethylindolium iodide (100 mg, 0.277 mmol) and the product from stage iv) (50 mg, 0.104 mmol) were dissolved in pyridine:acetic acid:acetic anhydride (9:9:2, 5 ml) and the reaction was stood at room temperature in the dark for 24 hours. After removing the solvents by a gentle nitrogen stream the residue was dissolved in water:acetonitrile (7:3, 5 ml) and the product was isolated by reverse phase HPLC. UV (methanol): λmax abs=652 nm, λmax em=670 nm. MS: m/z=621.2 (for C$_{33}$H$_{40}$N$_3$O$_7$S=622.8).

Example 2

Preparation of 2-{5-[1-(5-Carboxypentyl)-3,3-dimethyl-5-sulpho-1,3-dihydro-2H-indol-2-ylidene]-1,3-pentadienyl}-1-(3,5-dinitrobenzyl)-3,3-dimethyl-3H-indolinium, Salt (Compound II)

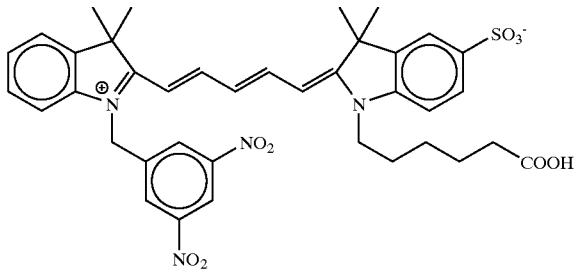

i) 1-(3,5-Dinitrobenzyl)-2,3,3-trimethylindolium iodide 3,5-Dinitrobenzyl chloride (100 mg, 0.46 mmol), 2,3,3-trimethylindole (74 μ, 73.2 mg, 0.46 mmol) and sodium iodide (69 mg, 0.46 mmol) were heated at 100° C. in sulpholane (5 ml) for 16 hours. After cooling to room temperature the product was isolated by reverse phase HPLC (89.7 mg, 0.26 mmol, 57% yield).

ii) 2-{5-[1-(5-Carboxypentyl)-3,3-Dimethyl-5-sulpho-1,3-dihydro-2H-indol-2-ylidene]-1,3-pentadienyl}-1-(3,5-dinitrobenzyl)-3,3-dimethyl-3H-indolinium, Salt (II)

N-(3,5-Dinitrobenzyl)-2,3,3-trimethylindolium iodide (20 mg, 0.059 mmol) and the product from Example 1 iv) (20 mg, 0.041 mmol) were dissolved in pyridine:acetic acid:acetic anhydride (2:2:1, 2.5 ml) and the reaction was allowed to stand in the dark at room temperature for 16 hours. The product was isolated by reverse phase HPLC to give 17.6 mg, 0.024 mmol, 59% yield of compound (II). MS: m/z=730 (for C$_{38}$H$_{41}$N$_4$O$_9$S=729.8.)

iii) 2{5[1-(5-Carboxypentyl)-3,3-Dimethyl-5-sulpho-1,3-dihydro-2H-indol-2-ylidene]-1,3-pentadienyl}-1-(3,5-dinitrobenzyl)-3,3-dimethyl-3H-indolinium, Salt, N-Hydroxysuccinimidyl Ester O-(N-Succinimidyl)-N,N,N',N'-bis-(tetramethylene)-uronium hexafluorophosphate (10 mg, 0.04 mmol) was dissolved in N,N-dimethylformamide (1 ml) and N,N-diisopropylethylamine (11 μl, 0.063 mmol) added. From this solution 100)1i was taken and added to the carboxylic acid (1 mg) from ii) above. After 3hrs, mass spectrum analysis indicated that the NHS ester had been formed. The product was used without further purification for labelling. MS: m/z=797 (for C$_{43}$H$_{49}$N$_4$O$_9$S=797.9).

Example 3

Preparation of 1-Butyl-2-{5-[1-(5-carboxypentyl)-3,3-dimethyl-6-sulpho-1,3-dihydro-2H-benzo[e]indol-2-ylidene[-1,3-pentadienyl}-3,3-dimethyl-5-nitro-3H-indolinium, Salt (Compound III)

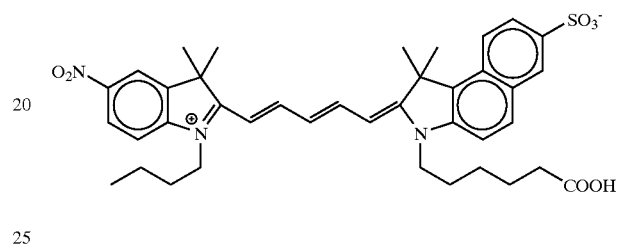

1-Butyl-5-nitro-2,3,3-trimethylindolium iodide (2.45 mg, 9.374 μmol) was added to 2-(2-anilinobutenyl)-1-(5-carboxypentyl)-3,3-dimethyl-6-sulpho-benz(e)indolium, salt (5 mg, 9.374 μmol) in pyridine:acetic acid:acetic anhydride (9:9:2; 200 μ). The reaction mixture was stored at room temperature in the dark for 4 days. The solvents were removed under reduced pressure and the residue was purified by reverse phase HPLC to give the desired product (2.0 mg, 2.854 μmol, 30% yield).

Example 4

Preparation of 1-Butyl-2-{7-[1-(5-carboxypentyl)3,3-dimethyl-5-sulpho-1,3-dihydro-2H-indol-2-ylidene]-1,3,5-heptatrienyl}-3,3-dimethyl-5-nitro-3H-indolinium, Salt (Compound IV)

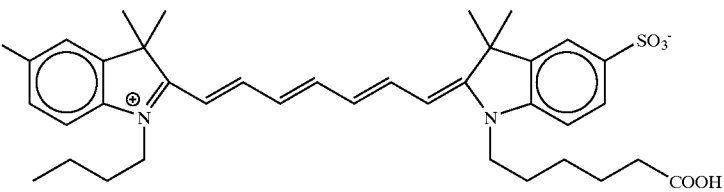

i) 1-Butyl-5-nitro-2,3,3-trimethylindolium Iodide

5-Nitro-2,3,3-trimethylindole (250 mg, 1.22 mmol) and iodobutane (10 ml, 16.17 g, 87.87 mmol) were mixed and heated to reflux for 16hrs. The solvent was removed and the impure material stored at–20° C. for use in later reactions.

ii) 1-Butyl-2-{7-[1-(5-carboxypentyl)3,3-dimethyl-5-sulpho-1,3-dihydro-2H-indol-2-ylidene)-1,3,5-heptatrienyl}-3,3-dimethyl-5-nitro-3H-indolium, Salt (IV)

1-(5-Carboxypentyl)-5-sulpho-2,3,3-trimethylindolium, salt (5 mg, 0.0141 mmol), 1-butyl-5-nitro-2,3,3-trimethylindolium iodide (4.02 mg, 0.0141 mmol) and N-[(5-phenylamino-)2,4-pentadienylidene]aniline monohydrochloride (3.69 mg, 0.0141 mmol) were dissolved in pyridine:acetic acid:acetic anhydride (9:9:2, 1 ml) and the reaction was allowed to stand at room temperature in the dark for 1 week. UV analysis at 752 nm over the week indicated the reaction was complete at the end of the week. The product was then isolated by reverse phase HPLC to give a blue solid (yield=4.3 mg, 45%). UV (methanol): λmax. abs=752 nm. MS: m/z=676 (for $C_{37}H_{46}N_3O_7S$= 676.9).

Example 5

Preparation of 2-{3-[1-(3-aminopropyl)-3,3-dimethyl-5-sulpho-1,3-dihydro-2H-indol-2-ylidene]-1-propenyl}-3-(3,5-dinitrobenzyl)-1,3-benzothiazol-3-ium, Salt (Compound V)

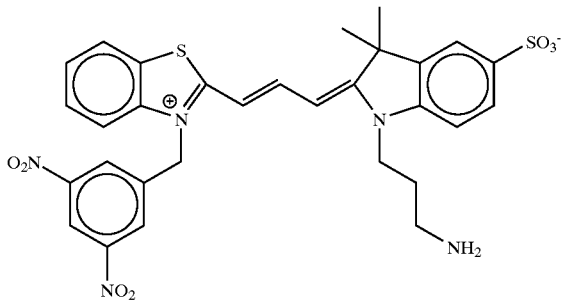

i) 3-(3,5-Dinitrobenzyl)-2-methyl-1,3-benzothiazol-3-ium Iodide 2-methylbenzothiazole (3 ml, 20.1 mmol) was dissolved in acetone (25 ml), to which was added 3,5-dinitrobenzyl iodide (7.4 g, 24.1 mmol) and heated with stirring to reflux for 15 hours. The reaction was allowed to cool and added drop-wise to ether (500 ml) to produce a fine yellow solid which was filtered and dried to constant weight in vacuo to give 3-(3,5-dinitrobenzyl)-2-methyl-1,3-benzothiazol-3-ium iodide (5 g, 10.9 mmol, 45% yield). MS: m/z=328 ($C_{15}H_{12}N_3O_4S$=330.3). $^1$H NMR (200 MHz-DMSO-$d_6$): δ 2.85 (s, 1 H); 3.7 (s, 3H); 6.35 (s, 2H); 7.37 (m, 2H); 8.23 (d, 1H); 8.53 (d, 1H); 8.62 (s, 2H): 8.8 (s, 1H).

ii) 1-(3-Aminopropyl)-2,3,3-trimethyl-5-sulpho-3H-indolium Bromide a) 2,3,3-Trimethylindolenium-5-sulphate (20 g, 84 mmol) and N-(3-bromopropyl)phthalimide (50 g, 186 mmols) were stirred in sulpholane (75 ml) at 110° C. for 28 hours. Further amounts of N-(3-bromopropyl)phthalimide (2.5 g, 84 mmol) were then added after 28 hours and after 45 hours. The reaction mixture was heated for a total of 65 hours then cooled and added to ethyl acetate (800 ml) forming a precipitate which was filtered and washed with ethyl acetate (3×300 ml) and acetonitrile (5×400 ml) to give a pink solid which was dried in vacuo to give 2,3,3-trimethyl-1-(3-phthalimidopropyl)-5-sulfo-indolium bromide (25 g, 49 mmols, 59% yield).

b) 2,3,3-Trimethyl-1-(3-phthaiimidopropyl)-5-sulpho-indolinium bromide (14 g, 27.6 mmols) was dissolved in concentrated HCl (100 ml) with methanol (50 ml). The reaction mixture was stirred at 100° C. for 32hrs. The reaction mixture was then cooled and the solvent removed under reduced pressure and dissolved in acetonitrile forming a precipitate. The solution was neutralised with concentrated ammonia (~10 ml) and the precipitate was filtered, dissolved in a minimum amount of water and purified by running the solution through a 2 g plug of C18 silica. The pink solid was freeze dried to give 1-(3-aminopropyl)-2 3,3-trimethyl-5-sulpho-3H-indolium bromide (8 g, 21.2 mmols, 77%yield).

UV (methanol): λmax=254 nm. MS: m/z=294 ($C_{14}H_{21}N_2O_3S$=297). $^1$H NMR (200 MHz-DMSO-$d_6$):δ1.5 (2s, 6H); 2.1 (m, 2H); 2.98 (s, 3H); 3.3 (m, 2H,); 3.6 (t, 2H); 6.6 (d, 1H, J=7.8 Hz); 7.5 (m, 2H); 8.2 (dd, 1H, J=4 and 6 Hz).

iii) Synthesis of Compound V

N,N'-Diphenylformamidine (236 mg, 1.2 mmol) was added to a solution of 3-(3,5-dinitrobenzyl)-2-methyl-1,3-benzothiazol-3-ium iodide (500 mg, 1.09 mmol) and 1-(3-aminopropyl)-2,3,3-trimethyl-5-sulpho-3H-indolium bromide (412.5 mg, 1.09 mmol) dissolved in pyridine (4.5 ml), acetic acid (4.5 ml) and acetic anhydride (1 ml). The reaction was heated at 100° C. for 3.5 hours then cooled to room temperature and purified by reverse phase HPLC. The pink solid isolated was then dissolved in aqueous hydrochloric acid (2.0M) and refluxed for 95 hours. The solution was then cooled to room temperature, evaporated and then re-purified by reverse phase HPLC. The pink solid collected was dried in vacuo. UV (ethanol): λmax=559 nm. MS: miz=638 ($C_{30}H_{30}N_5S_2O_7$=636.6).

Example 6

Preparation of 2-[3-(3-(5-Carboxypentyl)-1,3-benzothiazol-2(3H)-ylidene)-1 -propenyl]-3-(3,5-dinitrobenzyl)-1,3-benzothiazol-3-ium, Salt (Compound VI)

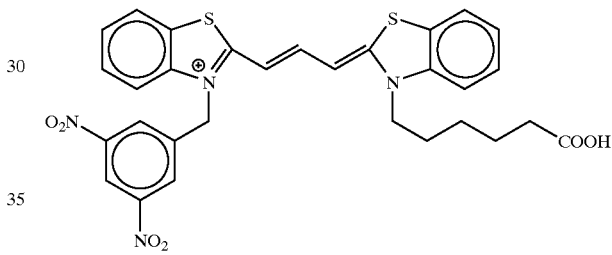

i) 3-(5-Carboxypentyl)-2-methyl-1,3-benxothiazol-3-ium bromide

To 2-methylbenzothiazole (80 ml, 93.849, 0.629mol) was added 6-bromohexanoic acid (250 g, 1.28mol). The reaction mixture was stirred at 140° C. for 24 hours. A yellow precipitate was formed. The reaction was allowed to cool, dissolved in methanol (350 ml) and added dropwise to ethyl acetate (2I). A beige precipitate was collected and washed with ethyl acetate (3×50 ml). The solid was then dried to constant weight in vacuo to give 3-(5-carboxypentyl)-2-methyl-1,3-benxothiazol-3-ium bromide (182.35 g 0.53mol, 84% yield). UV (methanol): λmax=237, 277 nm. MS: gave m/z=262 ($C_{14}H_{18}NO_{22}S$=264). $^1$H NMR (200 MHz-DMSO-$d_6$):β1.49 (m, 4H); 1.9 (m, 2H); 2.24 (t, 2HJ=6.35 Hz); 3.32 (s, 3H); 4.72 (t, 2HJ=7.81 Hz); 7.85 (m, 2H); 8.4 (dd, 2H, J=8.31 Hz).

ii) 2-(2-Anilinoethenyl)-3-(3,5-dinitrobenzyl)-1,3-benzothiazol-3-ium, Salt

N,N'-Diphenylformamidine (42.9 mg, 0.29 mmol) was added to 3-(3,5-dinitrobenzyl)-2-methyl-1,3-benzothiazol-3-ium iodide (100 mg, 0.29 mmol), (prepared as in Example 5 i)) and sodium acetate (excess) in ethanol (1 ml). The reaction was stirred at 40° C. for 4 hours to give a red solution. The solvent was removed under reduced pressure and the residue was purified by reverse phase HPLC to yield an orange gum.

iii) Synthesis of Compound VI 3-(5-Carboxypentyl)-2-methyl-1,3-benzothiazol-3-ium bromide (7.9 mg, 0.02 mmol) was added to 2-(2- anilinoethenyl)-3-(3,5-dinitrobenzyl)-1,3-benzothiazol-3-ium salt (10 mg, 0.02 mmol) and sodium acetate (excess) in ethanol (1 ml). The reaction was stirred at 45° C. and a pink solution was observed. The solvent was removed in vacuo and the residue was purified by reverse phase HPLC to yield a dark pink solid. UV (water/acetonitrile): λmax=558 nm. MS: m/z=604 ($C_{30}H_{27}N_4O_6S_2$=603.7).

Example 7

Preparation of 3-[4-(carboxymethyl)benzyl]-2-{3-[1-(3,5-dinitrobenzyl)-3,3-dimethyl-5-sulpho-1,3-dihydro-2H-indol-2-ylidene]-1-propenyl}-1,3-benzoxazol-3-ium, Salt (Compound VII)

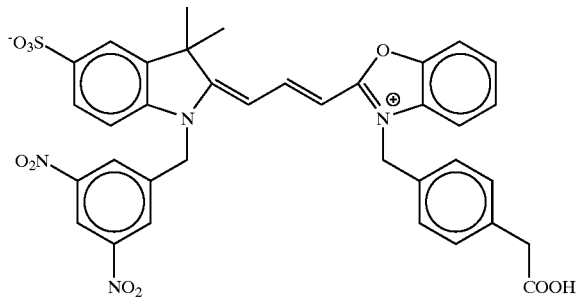

i) 3-[4-(Carboxymethyl)benzyl]-2-methyl-1,3-benzoxazol-3-ium Bromide

2-Methylbenzoxazole (yellow) was distilled under vacuum to give a colourless liquid (33 ml). 4-(Bromomethyl)phenylacetic acid (20 g, 87.3 mmol) and 2-methylbenzoxazole (distilled, 33 ml, 278 mmol) were dissolved in 1,2-dichlorobenzene (70 ml). The reaction mixture was heated at 80° C. for 2.5 days to produce a thick yellow precipitate. The reaction mixture was then cooled to room temperature, the precipitate collected via filtration and washed with 1,2-dichlorobenzene (3×100 ml) and diethyl ether (4×200 ml). The cream solid collected was dried in vacuo to give 3-(4-(carboxymethyl) benzyl]-2-methyl-1,3-benzoxazol-3-ium bromide (20 g, 55.3 mmol, 63% yield). UV (methanol): λmax=277 nm. MS: m/z=282 ($C_{17}H_{16}NO_3$=282.32). Normal phase TLC (ether) indicated that the starting 2-methylbenzoxazole had an $R_f$=0.9±0.05 and the product an $R_f$=0. $^1$H NMR (200 MHz-DMSO-d$_6$): δ1.75 (s, 2H); 3.2 (s, 3H); 5.85 (s, 2H); 7.31 (d, 2H, J=6.8 Hz); 7.53 (d, 2H, J=6.8 Hz); 7.72 (m, 2H, J=6.3 Hz); 7.89 (d, 1H, J=8.3 Hz); 8.17 (d, 1H, J=7.3 Hz); 9.8 (s, 1H).

ii) 1-(3,5-Dinitrobenzyl)-5-sulpho-2,3,3-trimethyl-3H-indolium Bromide 3,5-Dinitrobenzyl chloride (22.1g, 102 mmol) and sodium bromide (10.5 g, 102 mmol) were added to 2,3,3-trimethyl-5-sulpho-indole, potassium salt (5.0 g, 20.4 mmol) in sulpholane (25 ml). The reaction mixture was stirred at 100° C. for 5 hours. The solution was then cooled to room temperature and acetone (300 ml) was added to the reaction flask. A brown precipitate was formed which was collected by filtration and then purified by reverse phase HPLC. This gave a beige solid which was dried in vacuo. UV (water/acetonitrile): λmax=283 nm. MS: m/z=420 ($C_{18}H_{18}N_3O_7S$=420.4).

iii) 2-(2-Anilinoethenyl)-3-[4-(carboxymethyl)benzyl]-1,3-benzoxazol-3-ium, Salt Ethyl N-phenylformimidate (0.94 g, 6.27 mmol) was added to 3-[4-(carboxymethyl)benzyl]-2-methyl-1,3-benzoxazole-3-ium bromide (1.0 g, 2.76 mmol) dissolved in 2-methoxyethanol (10 ml) and heated at 100° C. for 1.5 hours. The solution was then cooled to room temperature and purified by reverse phase HPLC. The bright yellow solid obtained was dried in vacuo.

iv) Synthesis of Compound VII 1-(3,5-Dinitrobenzyl)-2,3,3-trimethyl-5-sulpho-3H-indolium bromide (130 mg, 0.26 mmol) was added to 2-(2-anilinoethenyl)-3-[4-(carboxymethyl)benzyl]-1,3-benzoxazol-3-ium bromide (100 mg, 0.26 mmol) dissolved in pyridine and acetic anhydride (20:0.6, 10 ml). The reaction was kept in the dark for 24 hours at room temperature. The solvent was then removed and the product was isolated after purification by reverse phase HPLC. UV (ethanol): λmax=512 nm. MS: m/z=714 ($C_{36}H_{31}N_4O_{10}S$=711.7).

Example 8

Preparation of 1-(5-Carboxypentyl)-2-[3-(1-(5-carboxypentyl)-3-methyl-5-nitro-1,3-dihydro-2H-benzimidazole-2-ylidene-1-propenyl)-3-methyl-5-nitro-3H-benzimidazol-1-ium, Salt (Compound VIII)

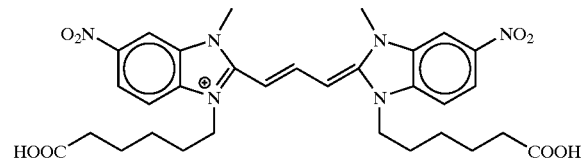

i) 1-(5-Carboxypentyl)-2,3-dimethyl-5-nitro-3H-benzimidazol-1-ium iodide

6-Iodohexanoic acid (6.33 g, 26.15 mmol) was added to 2,3-dimethyl-5-nitrobenzimidazole (1.0 g, 5.23 mmol) dissolved in sulpholane (10 ml) and stirred for 24 hours at 100° C. The reaction mixture was then cooled to room temperature and added dropwise to ethyl acetate (200 ml). A yellow precipitate was formed which was collected by filtration and dried in vacuo. This gave 1-(5-carboxypentyl)-2,3-dimethyl-5-nitro-3H-benzimidazol-1-ium iodide as a yellow solid (1.77 g, 4.09 mmol, 78% yield). UV (ethanol): λmax=285 nm. MS: m/z=306 ($C_{15}H_{20}N_3O_4$=306). Normal phase TLC (ethanol) indicated the starting material with $R_f$=0.6±0.05 and the product with $R_f$=O. $^1$H NMR (200 MHz-DMSO-d$_6$):β 2.3 (m, 8H); 2.95 (s, 3H); 4.0 (s, 3H); 4.6 (t, 2H); 8.24 (d, 1H, J=9.28 Hz); 8.5 (dd, 1H, J=9.28 and 1.95 Hz); 9.09 (d, 1H, J=1.95 Hz).

ii) 2-(2-Anilinoethenyl)-1-(5-carboxypentyl)-3-methyl-5-nitro-3H-benzimidazol-1-ium, salt Ethyl N-phenylformimidate (384.9 mg, 2.58 mmol) was added to 1-(5-carboxypentyl)-2,3-dimethyl-5-nitro-3H-benzimidazol-1-ium iodide (500 mg, 1.29 mmol) dissolved in 2-methoxyethanol (5 ml). The reaction was heated at 100° C. for 1 hour, cooled to room temperature and purified by reverse phase HPLC. The yellow solid was dried in vacuo for reacting further.

iii) Synthesis of Compound VIII 1-(5-Carboxypentyl)-2,3-dimethyl-5-nitro-3H-benzimidazol-1-ium iodide (9.4 mg, 0.024 mmol) was added to 2-(2-anilinoethenyl)-1-(5-carboxypentyl)-3-methyl-5-nitro-3H-benzimidazol-1-lium salt (10 mg, 0.024 mmol) dissolved in pyridine, acetic anhydride and triethylamine (20:0.6:0.7, 2 ml). The reaction was kept in the dark for 24 hours. The solvent was then evaporated and the product was isolated after purification by reverse phase HPLC. UV: λmax=535 nm. MS: m/z=622 ($C_{31}H_{37}N_6O_8$=621.6).

Example 9

Preparation of 2-{5-[1-(5-Carboxypentyl)-3,3-dimethyl-5,7-disulpho-1,3-dihydro-2H-benz[o]indol-2-ylidene]-1,3-pentadienyl}-3-(3,5-dinitrobenzyl)-1,3-benzothiazol-3-ium, Salt (Compound IX)

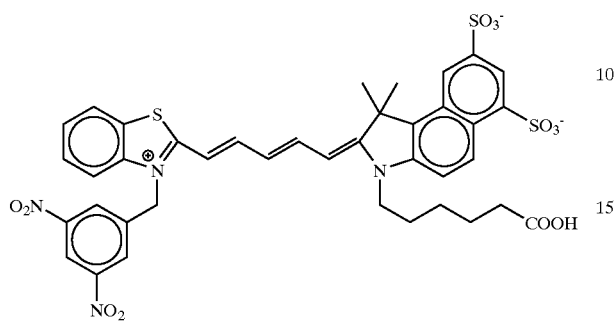

i) 1(5-Carboxypentyl)-2,3,3-trimethyl-5,7-disulpho-3H-benzo[e]indolium bromide

6-Bromohexanoic acid (30 g, 0.153mol) was added to 2,3,3-trimethyl-3H-benzo[e]indole-5,7-disulphonic acid (50 g, 0.112 mol) in nitrobenzene (200 ml) and stirred for 24 hours at 120° C. The reaction mixture was cooled to room temperature. A brown precipitate was formed which was collected by filtration and washed with 2-propanol (250 ml). The solid was then recrystallised from 2-propanol. The taupe solid was filtered and purified by reverse phase HPLC. This gave a grey solid which was dried in vacuo. UV (water/acetonitrile): $\lambda$max=273 nm, 283 nm. MS: m/z=484 ($C_{21}H_{26}NO_8S_2$=484.5). $^1$H NMR (200 MHz-DMSO-$d_6$): $\delta$ 1.7 (m, 14H); 2.2 t, 2H); 2.9 (s, 2H); 8.2 (d, 1H, J=9.28 Hz); 8.4 (d, 2H, J=4.39 Hz), 9.15 (d, 1H, J=9.28 Hz).

ii) Synthesis of Compound IX

Malonaldehydebisphenylimine monohydrochloride (141 mg, 0.55 mmol) was added to 1-(5-carboxypentyl)-2,3,3-trimethyl-5,7-disulpho-3H-benzo[e]indolium bromide (286 mg, 0.55 mmol) and 3-(3,5-dinitrobenzyl)-2-methyl-1,3-benzthiazole-3-ium iodide (200 mg, 0.55 mmol), (prepared as in Example 5 i)) dissolved in pyridine (18 ml), acetic acid (18 ml) and acetic anhydride (4 ml). The reaction was stirred at 80° C. for 4 hours and cooled to room temperature. The solvent was evaporated and the mixture was purified by reverse phase HPLC. The product, obtained as a blue solid, was dried in vacuo. UV (ethanol): $\lambda$max=676 nm. MS: m/z=853 ($C_{39}H_{37}N_4O_{12}S_3$=849.9).

Example 10

Preparation of 1-Butyl-2-[7-(3-(5-carboxypentyl)-1,3-benzothiazol-2-ylidene)-1,3,5-heptatrienyl]-3,3-dimethyl-5-nitro-3H-indolenium, Salt (Compound X)

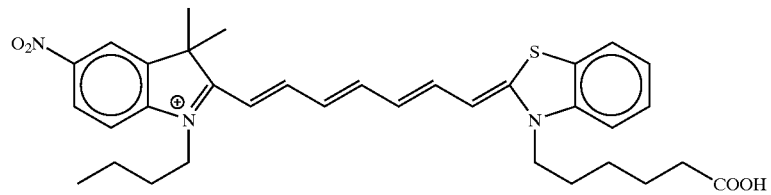

i) Synthesis of Compound X

N-[5-(Phenylamino)-2,4-pentadienylidene]aniline monohydrochloride (18 mg, 0.064 mmol) was added to 1-butyl-2,3,3-trimethyl-5-nitro-3H-indolium iodide (25 mg, 0.064 mmol) and 3-(5-carboxypentyl)-2-methyl-1,3-benzothiazol-3-ium bromide (22 mg, 0.064 mmol} in acetic acid (0.5 ml) and pyridine (0.5 ml). The reaction was heated at 40° C. for 4 hours. The solution was then cooled to room temperature and the solvent evaporated under reduced pressure. The dark green residue was dissolved in dimethyl sulphoxide and purified by reverse phase HPLC to yield a green solid. UV (methanol): $\lambda$max=768 nm. MS: m/z=587 ($C_{34}H_{40}N_3O_4S$=586.7).

Example 11

Preparation of 2-{5-[1-(5-Carboxypentyl)-3,3-dimethyl-5-sulpho-1,3-dihydro-2H-indol-2-ylidene]-1,3-pentadienyl}-1-(3,5-dinitrobenzyl)-3,3-dimethyl-5-sulfo-3H-indolium, Salt (Compound XI)

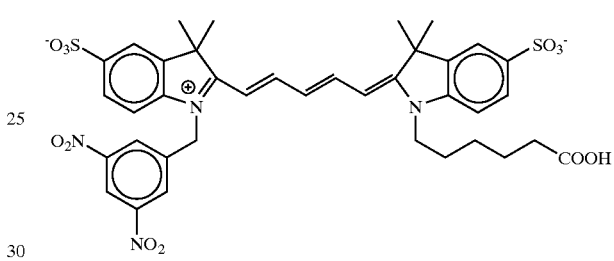

i) Synthesis of Compound XI

The reaction was carried out by an analogous method to that reported for Compound IX using 1-(3,5-dinitrobenzyl)-2,3,3-trimethyl-5-sulfo-3H-indolium bromide (50 mg, 0.12 mmol) and 1-(5-carboxypentyl)-2,3,3-trimethyl-5-sulfo-3H-indolium bromide (43 mg, 0.12 mmol) in the presence of malonaldehydebisphenylimine monohydrochloride (32 mg, 0.12 mmol) in acetic acid (0.9 ml), pyridine (0.9 ml) and acetic anhydride (0.2 ml). The product was isolated as a blue solid. UV (ethanol): $\lambda$max=651 nm. MS: m/z=811 ($C_{38}H_{41}N_4O_{12}S_2$=809.9).

Example 12

Relative Fluorescence Emission of Non-fluorescent Cyanine Dyes

Compounds V, VII, IX and XI were prepared as solutions in ethanol ($5 \times 10^5$M). For comparison, solutions of the fluorescent dyes Cy3 and Cy5 were prepared in ethanol at the same concentration. The fluorescence intensity of each of the dye solutions was measured using a fluorescence plate reader. Serial dilutions (1:1) with ethanol of all dye solutions were then made and the fluorescence intensity measured for each dilution. The fluorescence emission of the non-

Example 13

Nucleic Acid Hybridisation Assay

13.1 Probe Preparation

Oligonucleotide A (5'-C6-amino modifier-TAC CCA GAC GAG CAA-biotin-3') (SEQ ID No. 2) and the complementary oligonucleotide B (5'-TTG CTC GTC TGG GTA-C7-amino modifier-3') (SEQ ID No. 3) were synthesised on an Applied Biosystems 391 DNA synthesiser using standard methods and materials. The oligonucleotides were deprotected for 17 hours at 40° C. and purified by reverse phase HPLC using C18 column and a 40% TEAA/acetonitrile gradient. The desired peaks were collected, freeze dried and the samples were resuspended in sterile $H_2O$.

Oligonucleotides A and B were incubated with a 10-fold molar excess of Cy3 NHS-ester dye and 2-{5-[1-(5-carboxypentyl)-3,3-dimethyl-5-sulpho-1,3-dihydro-2H-indol-2-ylidene]-1,3-pentadienyl}-1-(3,5-dinitrobenzyl)-3,3-dimethyl-5-nitro-3H-indolinium salt (Compound II)-NHS-ester respectively, in 0.1 M sodium bicarbonate buffer (pH9), overnight at 22° C. The following morning, the oligonucleotides were precipitated using ethanol and the resulting pellets were resuspended in water. Labelled oligonucleotides were purified by reverse phase HPLC using a C18 column and a 60% TEAA/acetonitrile gradient and the desired peaks collected and freeze dried. Residues were resuspended into H20 and concentration of recovered material was determined.

A control oligonucleotide C (5'-TTG CTC GTC TGG GTA-Dabcyl-3') (SEQ ID No. 3) was synthesised as above. The DABCYL moiety was added using a 3'-Dabcyl cpg column. Following synthesis, oligonucleotide C was deprotected for 17 hours at 40° C. and purified by HPLC as described.

13.2 Binding Assay

Figure 2:
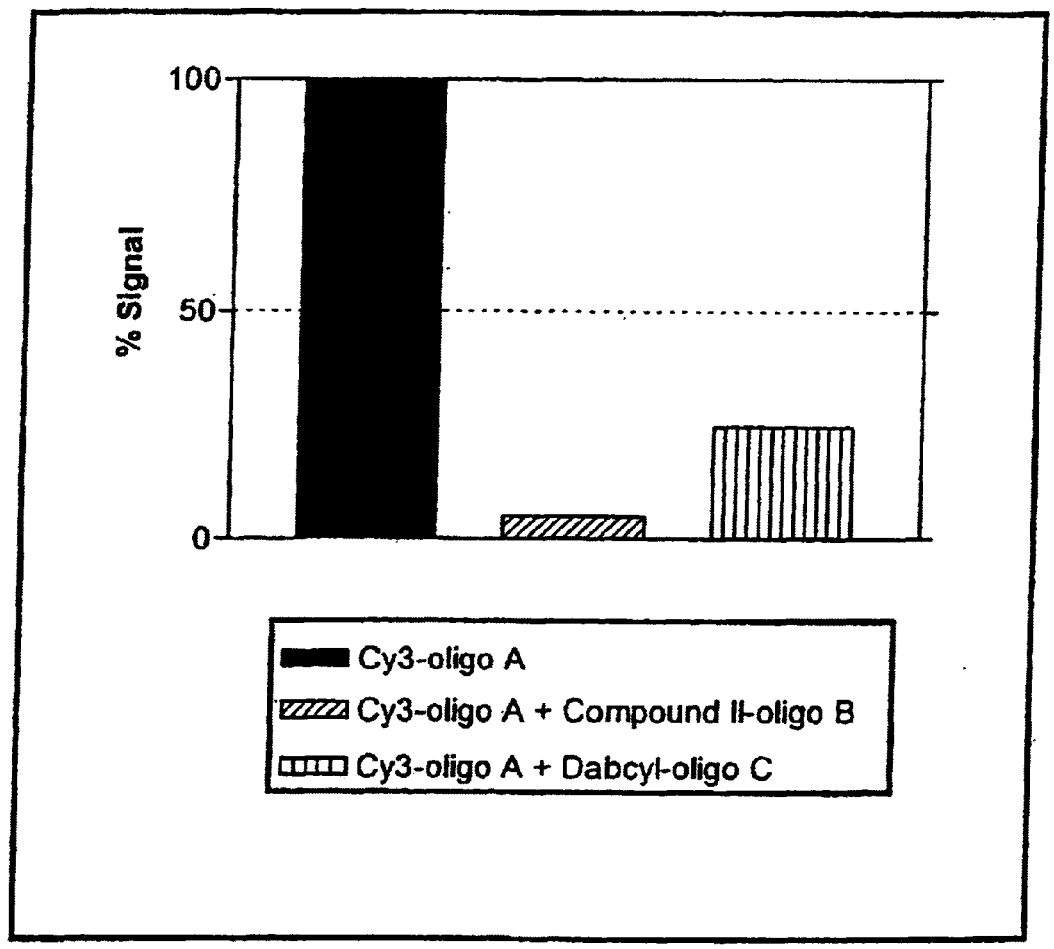
FIG. 2 illustrates nucleic acid hybridisation assays in which a reduction in fluorescence signal is observed, resulting from the binding of a Cy3-labelled oligonucleotide and its complementary oligonucleotide labelled with a non-fluorescent Cy5 analogue (Compound II) and with Dabcyl, according to Example 13.

Wells of a black, streptavidin-coated 96-well plate were coated with Cy3-labelled oligonucleotide A (100 pmol/well diluted in 100 µl $PBS/1MgCl_2$) for 120 minutes at ambient temperature. Any unbound material was removed by washing wells vigorously with buffer (PBS/1 mM $MgCl_2$/0.1% BSA). The Compound II-labelled oligonucleotide B and Dabcyl-labelled oligonucleotide C were diluted to 0.2 pmol/µl in buffer, and 100µl was incubated with the coated wells at ambient temperatures for 120 minutes. Wells were washed vigorously with PBS and fluorescence intensity was measured on a fluorescence plate reader using filter sets appropriate for Cy3. Signals from wells coated with Cy3-labelled oligonucleotide A alone were compared with those coated with Cy3-oligonucleotide A and incubated with either Compound II-labelled oligonucleotide B or control oligonucleotide C. The results are shown in FIG. 2. Wells coated with Cy3-oligonucleotide A, gave a strong fluorescence signal. This signal was reduced by 95% following hybridisation with Compound II-labelled oligonucleotide B and by 75% with oligonucleotide C.

Example 14

Figure 3:
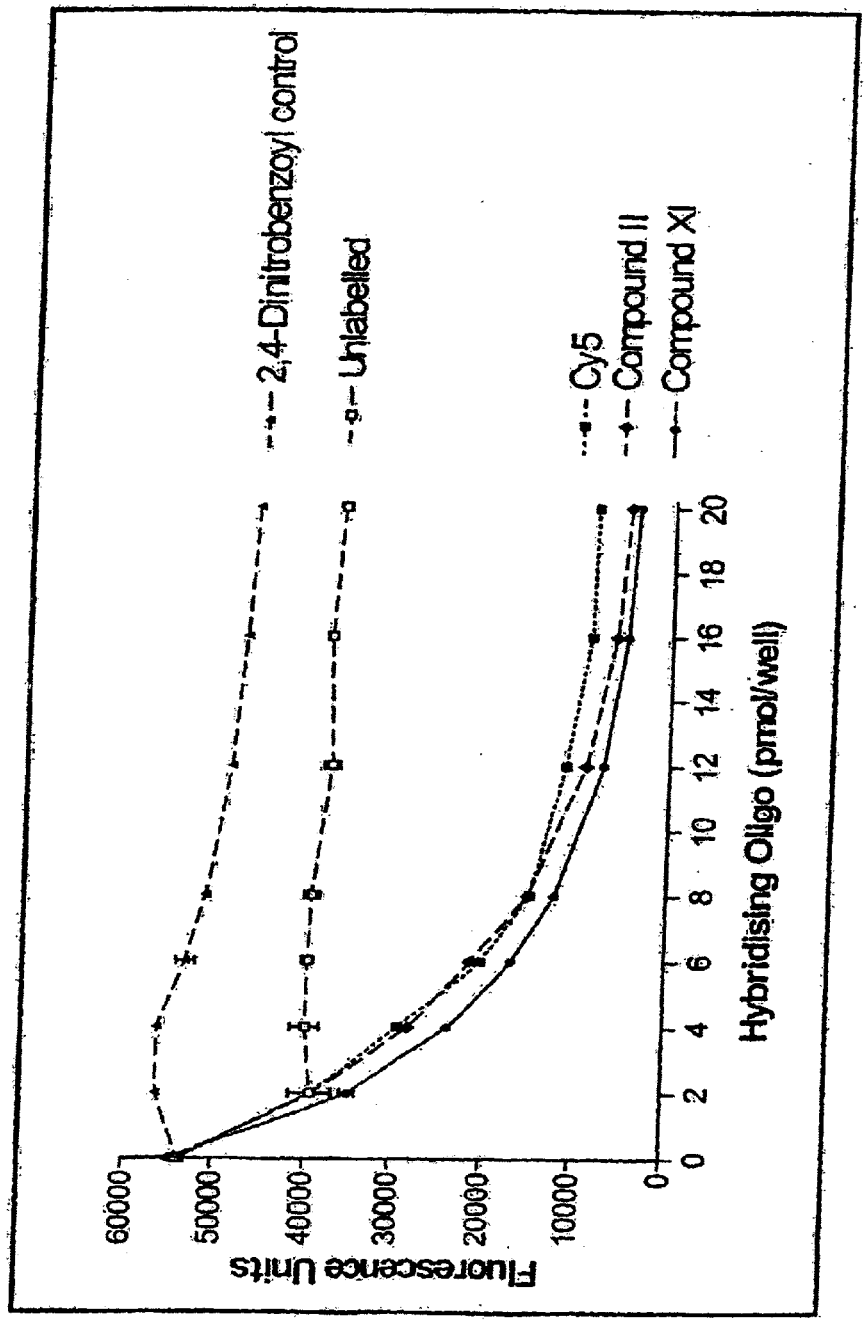
FIG. 3 illustrates the effect of using non-fluorescent cyanine dyes as acceptor dyes on signal to noise increase (and background reduction) compared with a standard matched fluorescent cyanine acceptor dye (Cy5) in an oligonucleotide hybridisation study according to Example 14.

Use of Non-fluorescent Cyanine Dyes Compared with a Standard Matched Fluorescent Cyanine Acceptor Dye (Cy5) in an Oligonucleotide Hybridisation Study An oligonucleotide (5'-TAC-CCA-GAC-GAG-CAA-3') (SEQ ID No. 2), labelled at the 3'-terminus with biotin and at the 5'-terminus with Cy3, was bound to the wells of a microtitre plate coated with streptavidin. The coated wells were then incubated with complimentary oligonucleotide probes labelled individually with non-fluorescent cyanine acceptor dyes (Compound II and Compound XI). Following hybridisation, the wells were washed and the relative fluorescence measured upon excitation of the Cy3 donor dye. Control measurements were made on complementary unlabelled-, CyS-labelled and 2,4-dinitrobenzoyl-labelled oligonucleotides. The results are shown in FIG. 3. The data indicates that the use of the non-fluorescent cyanine dyes (Compound II and Compound XI) is able to increase the signal to noise ratio by approximately a factor of 2 over that obtained with Cy5.

Example 15

Protease Cleavage Assay

15.1 Preparation of Protease Substrate

The peptide Ala-Ala-Phe-Phe-Ala-Ala-Lys (SEQ ID No. 1) was synthesised on a Perkin Elmer 433A peptide synthesizer using standard Fmoc chemistry. Cy5-NHS-ester dye (in slight molar excess) was coupled to the N-terminus of the peptide on the resin during overnight incubation in DMSO containing 2% v/v diisopropyl-ethylamine. The labelled peptide resin was washed sequentially with DMSO (~10 ml), methanol (~10 ml) and dichloromethane (~5 ml) and dried. A 90 minute incubation in 95%TFA/2.5% triisopropylsilane/2.5% $H_2O$ facilitated side-chain deprotection and cleavage from the resin. After filtering through glass wool the peptide was isolated as a blue precipitate in ice-cold diethylether. The product was re-suspended in DMSO and purified by reverse-phase HPLC (gradient: water+0.1%TFA to 70% MeCN+0.1%TFA), the desired fractions being collected and freeze-dried.

Cy5-Ala-Ala-Phe-Phe-Ala-Ala-Lys (SEQ ID No. 1) was incubated with 1-butyl-2-{5-[1-(5-carboxypentyl)-3,3-dimethyl-6-sulpho-1,3-dihydro-2H-benzo[e]indol-2-ylidene]-1,3-pentadienyl}-3,3-dimethyl-5-nitro-3H-indolinium salt (Compound III), NHS-ester, in slight molar excess in DMSO containing 2% v/v diisopropylethylamine overnight. The dual-labelled peptide was again isolated by reverse-phase HPLC and freeze-dried. The residue was re-suspended into $H_2O$ and the concentration determined.

15.2 Assay for Protease Enzyme

Figure 4:
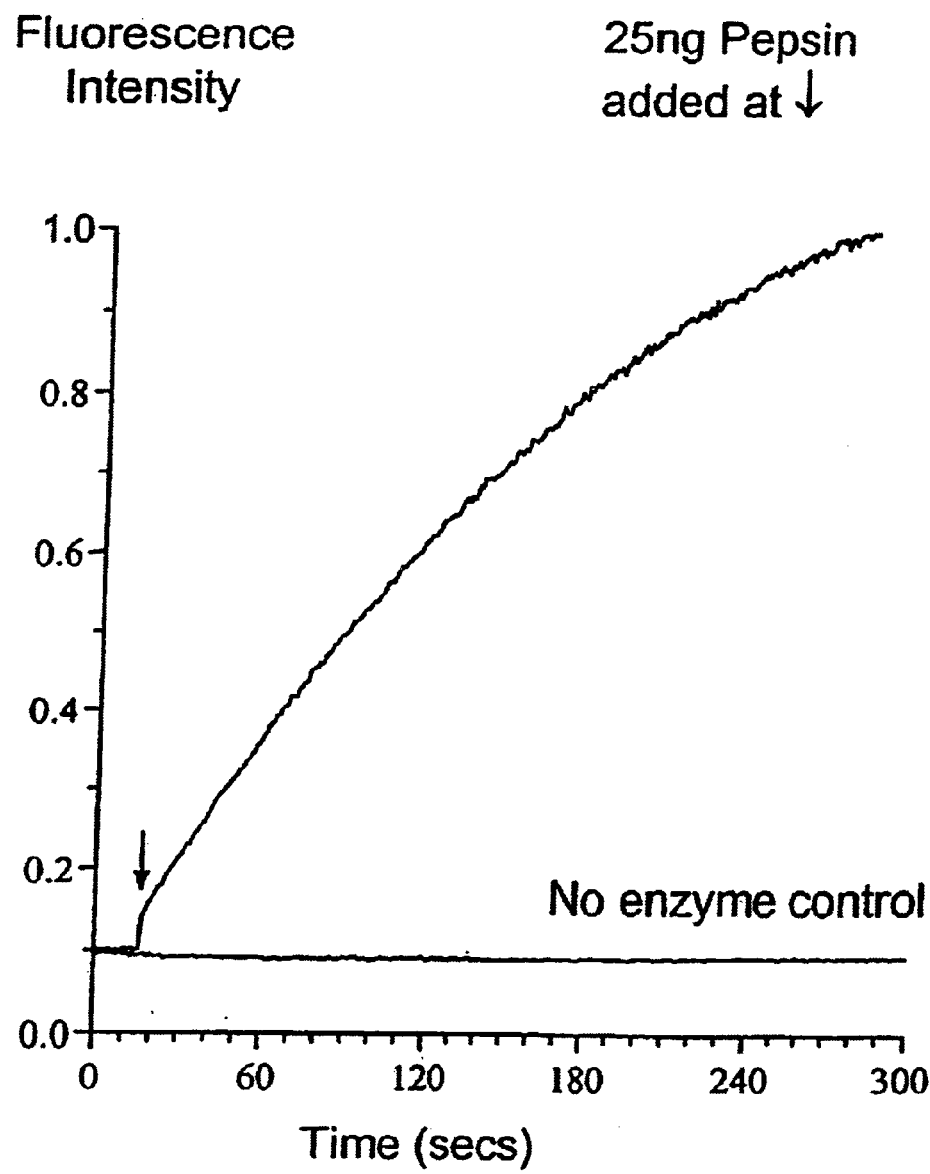
FIG. 4 illustrates the course of protease cleavage assays utilising the substrate, Cy5-Ala-Ala-Phe-Phe-Ala-Ala-Lys-Compound III (SEQ ID No. 1), in the presence and in the absence of pepsin, measured with respect to time and fluorescence intensity, according to Example 15

The protease substarte (Cy5-Ala-Ala-Phe-Phe-Ala-Ala-Lys-Compound III) Seq ID No 1) was diluted to 0.02 absorbance units/cm (at 650 nm) in citrate buffer (100 mM pH 3.0). To the solution (1 ml) of the labelled substrate in a cuvette, 25ng pepsin (10 µl volume) was added. The fluorescence baseline prior to protease addition and the subsequent increase in intensity were recorded at appropriate wavelengths. A control experiment (minus pepsin) was performed in a similar manner. The results are shown in FIG. 4. Efficient quenching of Cy5 fluorescence in the intact substrate results in a low signal. Protease-catalysed hydrolysis of the substrate removes this quenching, restoring the Cy5 fluorescence. The increase in fluorescence intensity can be continuously monitored and is proportional to protease activity.

What is claimed is:

1. A compound having the formula:

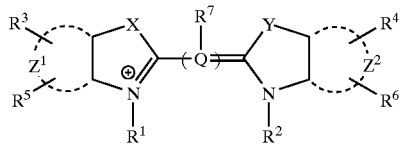

wherein the linker group Q contains at least one double bond and forms a conjugated system with the rings containing X and Y;

groups $R^3$, $R^4$, $R^5$ and $R^6$ are attached to the rings containing X and Y, or optionally, are attached to atoms of the $Z^1$ and $Z^2$ ring structures;

$Z^1$ and $Z^2$ each represent a bond or the atoms necessary to complete one or two fused aromatic rings each ring having five or six atoms, selected from carbon atoms and, optionally, no more than two oxygen, nitrogen and sulphur atoms;

X and Y are the same or different and are selected from bis-$C_1$–$C_4$ alkyl- and $C_4$–$C_5$ spiro alkyl-substituted carbon, oxygen, sulphur, selenium, —CH═CH— and N-W wherein N is nitrogen and W is selected from hydrogen, a group —$(CH_2)_m R^8$ where m is an integer from 1 to 26 and $R^8$ is selected from hydrogen, amino, aldehyde, acetal, ketal, halo, cyano, aryl, heteroaryl, hydroxyl, sulphonate, sulphate, carboxylate, substituted amino, quaternary ammonium, nitro, primary amide, substituted amide, and groups reactive with amino, hydroxyl, carbonyl, carboxyl, phosphoryl, and sulphydryl groups;

at least one of groups $R^1$, $R^2$, $R^3$, $R^4_1$, $R^5$, $R^6$ and $R^7$ is the group —E—F where E is a spacer group having a chain from 1–60 atoms selected from the group consisting of carbon, nitrogen, oxygen, sulphur and phosphorus atoms and F is a target bonding group;

any remaining groups $R^3$, $R^4$, $R^5$, $R^6$ and $R^7$ groups are independently selected from the group consisting of hydrogen, $C_1$–$C_4$ alkyl, $OR^9$, $COOR^9$, nitro, amino, acylamino, quaternary ammonium, phosphate, sulphonate and sulphate, where $R^9$ is selected from H and $C_1$–$C_4$ alkyl;

any remaining $R^1$ and $R^2$ are selected from $C_1$–$C_{10}$ alkyl which may be unsubstituted or substituted with phenyl the phenyl being optionally substituted by up to two substituents selected from carboxyl, sulphonate and nitro groups;

characterised in that at least one of the groups $R^1$, $R^2$, $R^3$, $R^4$, $R^5$, $R^6$ and $R^7$ comprises at least one nitro group which reduces the fluorescence emission of said compound such that it is essentially non-fluorescent;

provided that the linker group Q is not a squaraine ring system.

2. The compound according to claim 1 wherein Q contains 1, 2 or 3 double bonds in conjugation with the rings containing X and Y.

3. A compound having the formula:

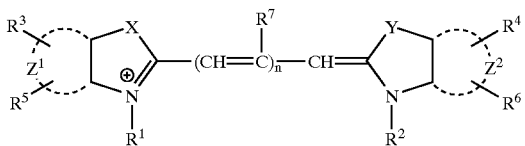

wherein groups $R^3$, $R^4$, $R^5$ and $R^6$ are attached to the rings containing X and Y or, optionally, are attached to atoms of the $Z^1$ and $Z^2$ ring structures and n is an integer from 1–3;

$Z^1$ and $Z^2$ each represent a bond or the atoms necessary to complete one or two fused aromatic rings each ring having five or six atoms, selected from carbon atoms and, optionally, no more than two oxygen, nitrogen and sulphur atoms;

X and Y are the same or different and are selected from bis-$C_1$–$C_4$ alkyl- and $C_4$–$C_6$ spiro alkyl-substituted carbon, oxygen, sulphur, selenium, —CH=CH— and N-W wherein N is nitrogen and W is selected from hydrogen, a group —$(CH_2)_m R^8$ where m is an integer from 1 to 26 and $R^8$ is selected from hydrogen, amino, aldehyde, acetal, ketal, halo, cyano, aryl, heteroaryl, hydroxyl, sulphonate, sulphate, carboxylate, substituted amino, quaternary ammonium, nitro, primary amide, substituted amide, and groups reactive with amino, hydroxyl, carbonyl, carboxyl, phosphoryl, and sulphydryl groups;

at least one of groups $R^1$, $R^2$, $R^3$, $R^4$, $R^5$, $R^6$ and $R^7$ is the group —E—F where E is a spacer group having a chain from 1–60 atoms selected from the group consisting of carbon, nitrogen, oxygen, sulphur and phosphorus atoms and F is a target bonding group;

any remaining groups $R^3$, $R^4$, $R^5$, $R^6$ and $R^7$ groups are independently selected from the group consisting of hydrogen, $C_1$–$C_4$ alkyl, $OR^9$, $COOR^9$, nitro, amino, acylamino, quaternary ammonium, phosphate, sulphonate and sulphate, where $R^9$ is selected from H and $C_1$–$C_4$ alkyl; any remaining $R^1$ and $R^2$ are selected from $C_1$∝$C_{10}$ alkyl which may be unsubstituted or substituted with phenyl the phenyl being optionally substituted by up to two substituents selected from carboxyl, sulphonate and nitro groups;

characterised in that at least one of the groups $R^1$, $R^2$, $R^3$, $R^4$, $R^5$, $R^6$ and $R^7$ comprises at least one nitro group which reduces the fluorescence emission of saiiik compound such that it is essentially non-fluorescent.

4. The compound according to claim 1 wherein the spacer group E is selected from:

—$(CHR')_p$—
—$\{(CHR')_q$—O—$(CHR')_r$—$\}_s$—
—$\{(CHR')_q$—NR'—$(CHR')_r\}_s$—
—$\{(CHR')_q$—(CH=CH)—$(CHR')_r\}_s$—
—$\{(CHR')_q$—Ar—$(CHR')_r$—$\}_s$—
—$\{(CHR')_q$—CO—NR'—$(CHR')_r$—$\}_s$—
—$\{(CHR')_q$—CO—Ar—NR'—$(CHR')_r$—$\}_s$— where R' is hydrogen, or $C_1$–$C_4$ alkyl which may be optionally substituted with sulphonate, Ar is phenylene, optionally substituted with sulphonate, p is 1–20, preferably 1–10, q is 1–5, r is 0–5 and s is 1–5.

5. The compound according to claim 1 wherein said target bonding group comprises a reactive group for reacting with a functional group on a target material, or a functional group for reacting with a reactive group on a target material.

6. The compound of claim 5 wherein said reactive group is selected from carboxyl, succinimidyl ester, sulphosuccinimidyl ester, isothiocyanate, imaleimide, haloacetamide, acid halide, hydrazide, vinylsulphone, dichlorotriazine and phosphoramidite.

7. The compound of claim 5 wherein said functional group is selected from hydroxy, amino, sulphydryl, imidazole, carbonyl including aldehyde and ketone, phosphate and thiophosphate.

8. The compound according to claim 1 wherein at least one of the groups $R^3$, $R^4$, $R^5$, $R^6$ and $R^7$ is a nitro group and/or at least one of the groups $R^1$ and $R^2$ is a mono- or di-nitro-substituted benzyl group.

9. A biological material labelled with the compound of claim 1.

10. A biological material which comprises two components one of which is labelled with a fluorescent dye which may act as a donor of resonance energy and the other with a non-fluorescent cyanine dye according to claim 1 and which may act as an acceptor of resonance energy transferred from the donor.

11. A biological material according to claim 9 selected from the group consisting of antigen, antibody, lipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl, hydroxyl and carboxyl, phosphate and thiophosphate groups, microbial materials, drugs and toxins.

12. A method for labelling a biological material comprising:

i) adding to a liquid which contains a biological material selected from the group consisting of an antigen, antibody, lipid, protein, peptide, carbohydrate, nucleotides, microbial materials, drugs, toxins and combinations thereof a compound according to claim 1, ii) reacting said compound with said biological material wherein said compound covalently binds to and labels said biological material.

13. An assay method which comprises:
i) separating two components which are in an energy transfer relationship, the first component being labelled with a fluorescent donor dye and the second component being labelled with a non-fluorescent cyanine acceptor dye according to claim 1 and,
ii) detecting the presence of the first component by measuring emitted fluorescence.

14. A method according to claim 13 wherein the assay is selected from proteolytic enzyme cleavage assays and nuclease enzyme cleavage assays.

15. An assay method which comprises:
i) binding one component of a specific binding pair with a second component of said pair, said first component being labelled with a fluorescent donor dye and said second component being labelled with a non-fluorescent cyanine acceptor dye according to claim 1 so as to bring about an energy transfer relationship between said first and second components; and,
ii) detecting the binding of the first and second components by measuring emitted fluorescence.

16. A method according to claim 15 wherein said specific binding pair is selected from the group consisting of antibodies/antigens, lectins/glycoproteins, biotin/(strept) avidin, hormone/receptor, enzyme/substrate or co-factor, DNA/DNA, DNA/RNA and DNA/binding protein.

17. A method according to claim 15 wherein said binding assay is selected from the group consisting of immunoassays, nucleic acid hybridisation assays, protein binding assays, hormone receptor binding assays and enzyme assays.

18. A biological material according to claim 10 selected from the group consisting of antigen, antibody, lipid, protein, peptide, carbohydrate, nucleotides which contain or are derivatized to contain one or more of an amino, suphydryl, carbonyl, hydroxyl and carboxyl, phosphate and thiophosphate groups, and oxy or deoxy polynucleic acids which contain or are derivatized to contain one or more of an amino, suphydryl, carbonyl, hydroxyl and carboxyl, phosphate and thiophosphate groups, microbial materials, drugs and toxins.

* * * * *

UNITED STATES PATENT AND TRADEMARK OFFICE
CERTIFICATE OF CORRECTION

PATENT NO. : 6,828,116 B1
DATED : December 7, 2004
INVENTOR(S) : Hamilton et al.

It is certified that error appears in the above-identified patent and that said Letters Patent is hereby corrected as shown below:

Title page,
Item [22], should read -- [22]  PCT Filed:  Jun. 2, 1999 --
Item [30], should read -- [30]  Foreign Application Pirority Data
             Jun. 11, 1998      (GB).......................... 9812596.6 --

Signed and Sealed this

Twenty-fifth Day of January, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,828,116 B1 | |
| APPLICATION NO. | : 09/719016 | |
| DATED | : December 7, 2004 | |
| INVENTOR(S) | : Hamilton et al. | |

It is certified that error appears in the above-identified patent and that said Letters Patent is hereby corrected as shown below:

Column 25,
Line 42, change "C1 ∞C10 alkyl" to --$C_1$–$C_{10}$ alkyl --. [note the numbers 1 and 10 are subscript]

Column 25,
Line 48, change "saiiik" to -- said --.

Signed and Sealed this

Twenty-third Day of January, 2007

JON W. DUDAS
*Director of the United States Patent and Trademark Office*